(12) United States Patent
Backers

(10) Patent No.: US 6,505,070 B1
(45) Date of Patent: Jan. 7, 2003

(54) DUAL-CHAMBER CARDIAC PACEMAKER

(75) Inventor: Jos Backers, Oudenburg (BE)

(73) Assignee: Biotronik Mess-und Therapiegerate GmbH & Co, Ingenieurburo Berlin, Berlin (DE)

( * ) Notice: Subject to any disclaimer, the term of this patent is extended or adjusted under 35 U.S.C. 154(b) by 0 days.

(21) Appl. No.: 09/464,735

(22) Filed: Dec. 15, 1999

(30) Foreign Application Priority Data

Dec. 15, 1998 (DE) .......................................... 198 59 651

(51) Int. Cl.$^7$ ............................................... A61N 1/362
(52) U.S. Cl. .......................................................... 607/9
(58) Field of Search ............................. 607/4, 5, 7, 14

(56) References Cited

U.S. PATENT DOCUMENTS

| | | | |
|---|---|---|---|
| 4,467,810 A | 8/1984 | Vollmann | 128/419 |
| 5,226,415 A | 7/1993 | Girodo et al. | 128/419 |
| 5,713,928 A | 2/1998 | Bonnet et al. | 607/9 |
| 5,931,856 A | 8/1999 | Bouhour et al. | 607/9 |

FOREIGN PATENT DOCUMENTS

| | | |
|---|---|---|
| EP | 0 488 840 | 6/1992 |
| EP | 0 677 303 | 10/1995 |
| EP | 0 714 676 | 6/1996 |
| EP | 0 755 696 | 1/1997 |
| EP | 0 845 282 | 6/1998 |
| WO | WO 97/43002 | 11/1997 |

*Primary Examiner*—George R. Evanisko
(74) *Attorney, Agent, or Firm*—Christie, Parker & Hale, LLP

(57) ABSTRACT

A dual-chamber cardiac pacemaker having a stimulation control unit for time control of the production and output of the stimulation pulses, and a method of operating the pacemaker according to the current invention are provided. The pacemaker comprising switching means for switching over from an asynchronous to a vestibule-synchronous mode, criterion memory means for storage of at least one switching-over criterion for mode switching-over, and a processing unit for processing signals from the atrium sensing means and the ventricle sensing means and the timer for checking fulfilment of the switching-over criterion, wherein the criterion memory means has a signal sequence memory for storage of a predetermined selection of signal sequence patterns reflecting an electrical activity of the heart and the processing unit has comparison means for comparison of the electrical activity detected by the atrium sensing means and the ventricle sensing means in a plurality of successive cardiac cycles to the stored signal sequence patterns and the stimulation control unit further has counting means connected to the comparison means on the input side for counting the number of cardiac cycles in which identity of the detected electrical activity was established with one of the pre-stored signal sequence patterns, within a predetermined total number of successive cardiac cycles.

8 Claims, 5 Drawing Sheets

DUAL-CHAMBER CARDIAC PACEMAKER

CROSS-REFERENCE TO RELATED APPLICATIONS

This application claims priority to German application serial number 198 59 651.0, filed Dec. 15, 1998.

FIELD OF INVENTION

The invention concerns generally to dual-chamber cardiac pacemakers, and more particularly to dual-chamber pacemakers having both atrium-synchronous and asynchronous modes of operation.

BACKGROUND OF THE INVENTION

Dual-chamber cardiac pacemakers which stimulate the ventricle synchronously with respect to atrial events are well-known in the art. Often these pacemakers are dual-mode and have a mode-switch function that switches the pacemaker from an atrium-synchronous to an asynchronous mode of operation, in the event that an upper limit rate of detected atrial cardiac actions is exceeded.

The reverse procedure, namely changing from an asynchronous to an atrium-synchronous mode of operation, i.e., termination of mode-switch episodes, is normally triggered by the detection of what is known as the 'x out of y-criterion'. The 'x out of y-criterion' occurs when the number of atrially detected events within a predetermined total number of atrial events occur at a rate below the upper atrial limit rate.

However, two serious errors can occur in re-synchronization of the ventricular stimulation pulses to the atrially detected events. Firstly, the atrially detected events can result from the retrograde transfer of ventricular stimulation pulses. In that case, each ventricularly stimulated event causes a retrograde-transfer atrial event, which in turn triggers an AV-time, after which there is simulated a ventricular event which again causes a retrograde-transfer atrial event, and so forth. In such a case, re-synchronization to the atrially detected events would result in synchronization to the ventricle stimuli and directly trigger pacemaker mediated tachycardia (PMT).

Secondly, the atrially detected rate can result from a 2:1-detection of atrial events on the basis of atrial blanking, which makes each second atrial event 'invisible' for the pacemaker. In such a case, re-synchronization would then directly result in the 2:1-block behaviour which is highly undesirable from a physiological point of view.

Attempts have been made to design around the re-synchronization problem. For example, U.S. Pat. No. 5,549,648 describes a pacemaker system and an operating procedure for the improved detection of the end phase of a retrograde transfer. The aim of the '648 device is to provide a system capable of analyzing atrial and ventricular cardiac actions on a beat-to-beat basis by reference to given criteria (referred to as 'beat-to-beat' analysis). On the basis of that analysis, the operation of the pacemaker is then to be re-synchronized. However, the re-synchronization errors described above are not eliminated with the procedure of the '648 patent. On the contrary, the system disclosed in the '648 patent is only concerned with the fastest possible detection of the condition in which the mode switch episode can be concluded. Indeed, the aim of the '648 patent, to expediently initiate re-synchronization, tends to make checking the analysis result and eliminating re-synchronization errors impossible.

Accordingly, a need exists for a dual-chamber cardiac pacemaker capable switching back from an asynchronous to an atrium-synchronous mode and re-synchronization of the pacemaker to the atrium in such a way as to substantially exclude malfunctions.

SUMMARY OF THE INVENTION

The present invention is direct to a dual-chamber pacemaker designed to avoid errors in the switching-back and re-synchronization procedures. Generally, the dual-chamber pacemaker comprises: a programming device, a body sensor, an atrium electrode, and a ventricle electrode. An internal telemetry may be further provided for connecting the implanted pacemaker to the programming device and a stimulation control unit may be provided for operational control. In such an embodiment, the stimulation control unit generally comprises an internal program memory, a data memory, and a clock and timer.

Any suitable body sensor may be utilized in the current invention. For example, the body sensor may include one or more of the following: a piezoelectric activity sensor, a sensor for blood oxygen saturation or blood temperature, or an impedance plethysmograph.

In one embodiment, a ventricle sensing unit and a ventricle stimulation unit are connected to the ventricle electrode, and similarly an atrium sensing unit and an atrium stimulation unit are connected to the atrium electrode. In such an embodiment, the sensing units may be connected to data inputs of the stimulation control unit and the stimulation units may be connected to control signal outputs thereof.

In another embodiment, the invention is also directed to a method of utilizing the dual-chamber pacemaker. In such an embodiment, the method of operation comprised the following steps: a) a counter used to detect fulfilment of the x-out of-y-criterion ('x-out of-y-counter') is incremented only at the occurrence of certain known sequences of cardiac events (hereinafter also referred to as 'signal sequence patterns'); b) if the counter condition satisfies a predetermined x-out of-y-criterion, in particular in the form of modulation or variation of a plurality of ventricularly detected or stimulated events (V), such as a V-V-interval—a test is carried out for the presence of a retrograde transfer. If the interval between the V and atrially detected events (As), or V-AS, respectively following modulation are of a constant duration, the situation entails retrograde transfer. If, in contrast, the moment in time at which atrially detected events occur is independent of the (varied) moment in time of ventricular stimulation, the events were not retrogradedly transferred.

In yet another alternative embodiment, the event sequences detected for include: As-V-As wherein As-As>1.000 ms; V-As-As-V wherein As-As>1.000 ms; V-V-As wherein V-As>1.000 ms; and V-V without interposed As.

In still another alternative embodiment, modulation is desirably implemented in the form of a prolongation of the time intervals by a post-ventricular atrial blanking time. In such an embodiment an additional increment and re-synchronization is activated if at least three successive V-As-time intervals were constant after modulated ventricle stimuli.

In still yet another embodiment of the invention, the criterion memory is adapted for the storage of at least one rate threshold value concerning the time intervals between successive atrial activities—preferably for the storage of two different threshold values in different stages of the test procedure—and the processing unit has a calculating unit for ascertaining the current atrial time intervals or atrial rate and (at least) one rate comparison unit for comparison thereof with the stored rate threshold value. The result of the rate comparison is then passed to a logic stage, together with the result of the x-out of-y-counting operation. In such an embodiment, activation of the switching means for switching over into the synchronous mode and re-synchronization of ventricle stimulation is made dependent not only on the result of the logical processing operation, but presupposing attainment of the counter condition 'x' by the counter means, on the additional presence of an output signal from the rate comparison unit which indicates when the atrial rate falls below a predetermined threshold value ('decision rate'). In accordance with the foregoing, in one such embodiment, the logic stage implements AND-gating of the x-out of-y-counting procedure and the additional test by modulation of the W-stimulation interval, which is preceded in particular also by OR-gating between the test result and the rate comparison.

In still yet another embodiment, the stimulation control unit desirably effects dynamic rate limitation, i.e., the ventricular stimulation rate, for avoiding PMT ('dynamic PMT limit'). In connection with such an embodiment, the stimulation function is further designed such that the specific rate limit value is selected based on the result of the test steps provided: 1) if in the outcome of the tests pacemaker operation is set to atrial sine rhythm (spontaneous atrial rate>sensor-indicated rate), the rate limitation should be based on the rate of spontaneous atrial activity ('sine rate'); and 2) if, however, the preceding tachycardia leads into atrial bradycardia (spontaneous atrial rate<sensor-indicated rate), the limit rate should be derived from the sensor-indicated rate. These conditions also apply where retrograde transfer was established and active re-synchronization was implemented.

BRIEF DESCRIPTION OF THE DRAWINGS

Advantageous developments of the invention are also characterized in the appendant claims or are set forth hereinafter in greater detail together with the description of the preferred embodiment of the invention, with reference to the drawings in which:

DETAILED DESCRIPTION OF THE INVENTION

Figure 1:
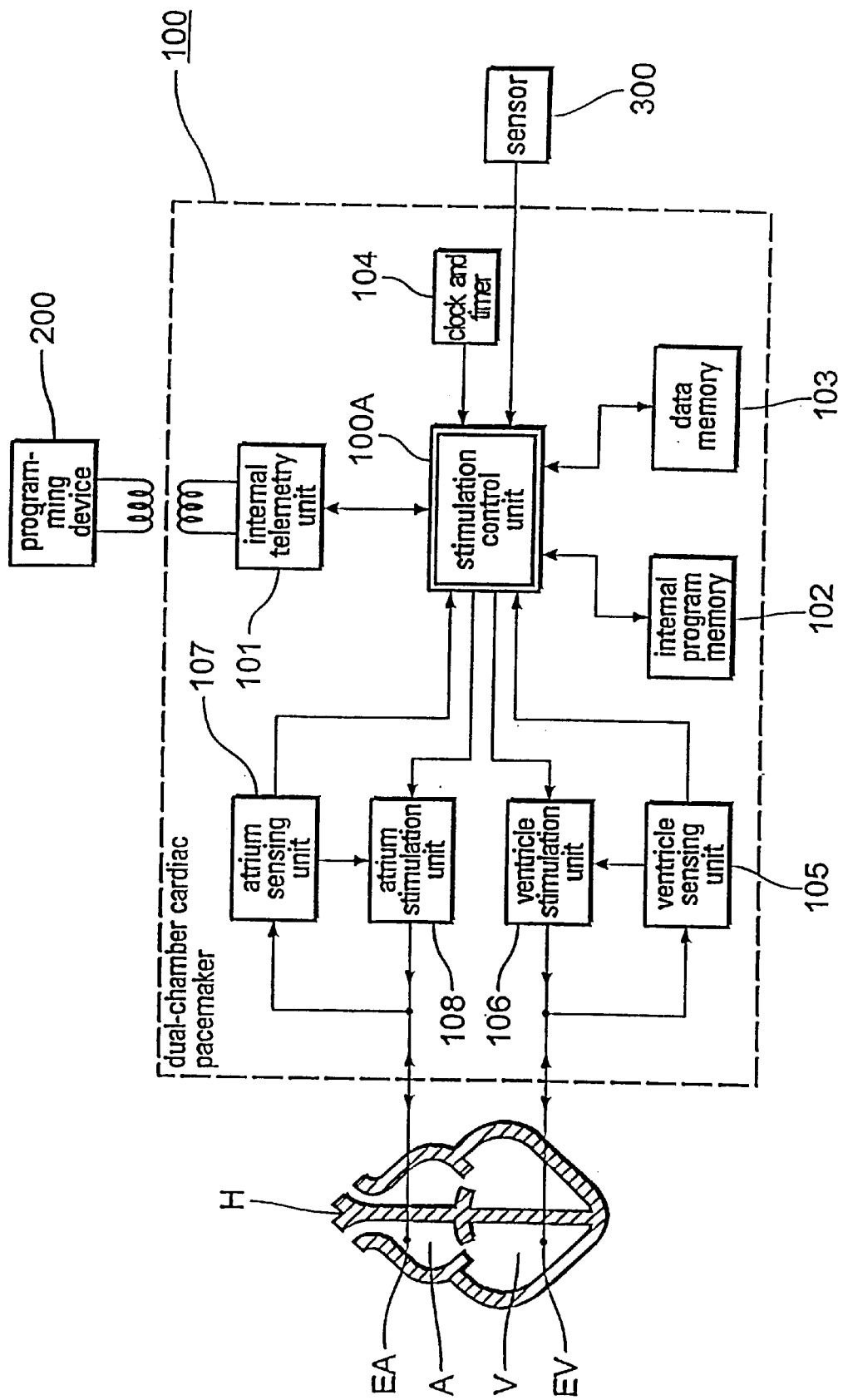
FIG. 1 shows a functional block circuit diagram of a dual-chamber pacemaker in accordance with an embodiment of the invention.

A dual-chamber pacemaker designed to avoid errors in the switching-back and re-synchronization procedures is disclosed herein. Generally, the dual-chamber pacemaker comprises: a programming device, a body sensor, an atrium electrode, and a ventricle electrode. FIG. 1 shows a schematic diagram of the components of a pacemaker apparatus comprising: a dual-chamber cardiac pacemaker 100, a programming device 200, a body sensor 300, an atrium electrode EA in the atrium A and a ventricle electrode EV in the ventricle V of a heart H. An internal telemetry unit 101 is provided for connecting the implanted pacemaker 100 to the programming device 200 and a stimulation control unit 100A is provided for operational control.

Associated with the stimulation control unit 100A in the usual manner are an internal program memory 102, a data memory 103, as well as a clock and timer 104. The body sensor 300 is connected to an input of the stimulation control unit 100A. Any suitable body sensor 300 may be utilized, such as, for example, a piezoelectric activity sensor, a sensor for blood oxygen saturation or blood temperature or an impedance plethysmograph.

Connected to the ventricle electrode EV on the input side is a ventricle sensing unit 105, and on the output side a ventricle stimulation unit 106. Similarly, connected to the atrium electrode EA on the input side is an atrium sensing unit 107, and on the output side an atrium stimulation unit 108. The sensing units 105 and 107 are connected to data inputs of the stimulation control unit 100A and the stimulation units 106 and 108 are connected to control signal outputs thereof.

The dual-chamber pacemaker 100 of the current invention is designed to operate in a rate-adaptive dual-chamber demand mode on the basis of rate control signals which—on the basis of a programmed algorithm, which may be controlled by way of the programming device 200—are formed on the basis of signals from the body sensor 300 in the stimulation control unit 100A and fed to the stimulation units 106 and 108. The pacemaker 100 is further designed for switching between an atrium-synchronous mode to an asynchronous mode during episodes of vestibule flutter and for switching back into the synchronous mode upon the termination of such episodes on the basis of specific criteria or tests.

In one embodiment, the switching-back procedure utilized for a pacemaker 100 according to the present invention is accomplished when, for a predetermined number of cardiac cycles from a set total number of cardiac cycles, one of a predetermined set of signal sequence patterns or indices for the termination of atrial tachycardia is detected. An exemplary set of signal sequence patterns is set forth in Table 1, below.

TABLE 1

Exemplary Signal Sequence Patterns

| Sequence | Conditions |
| --- | --- |
| As—V—As | As—As > 1.000 ms |
| V—As—As—V | As—As > 1.000 ms |
| V—V—As wherein | V—As > 1.000 ms |
| V—V | without interposed As |

Figure 2:
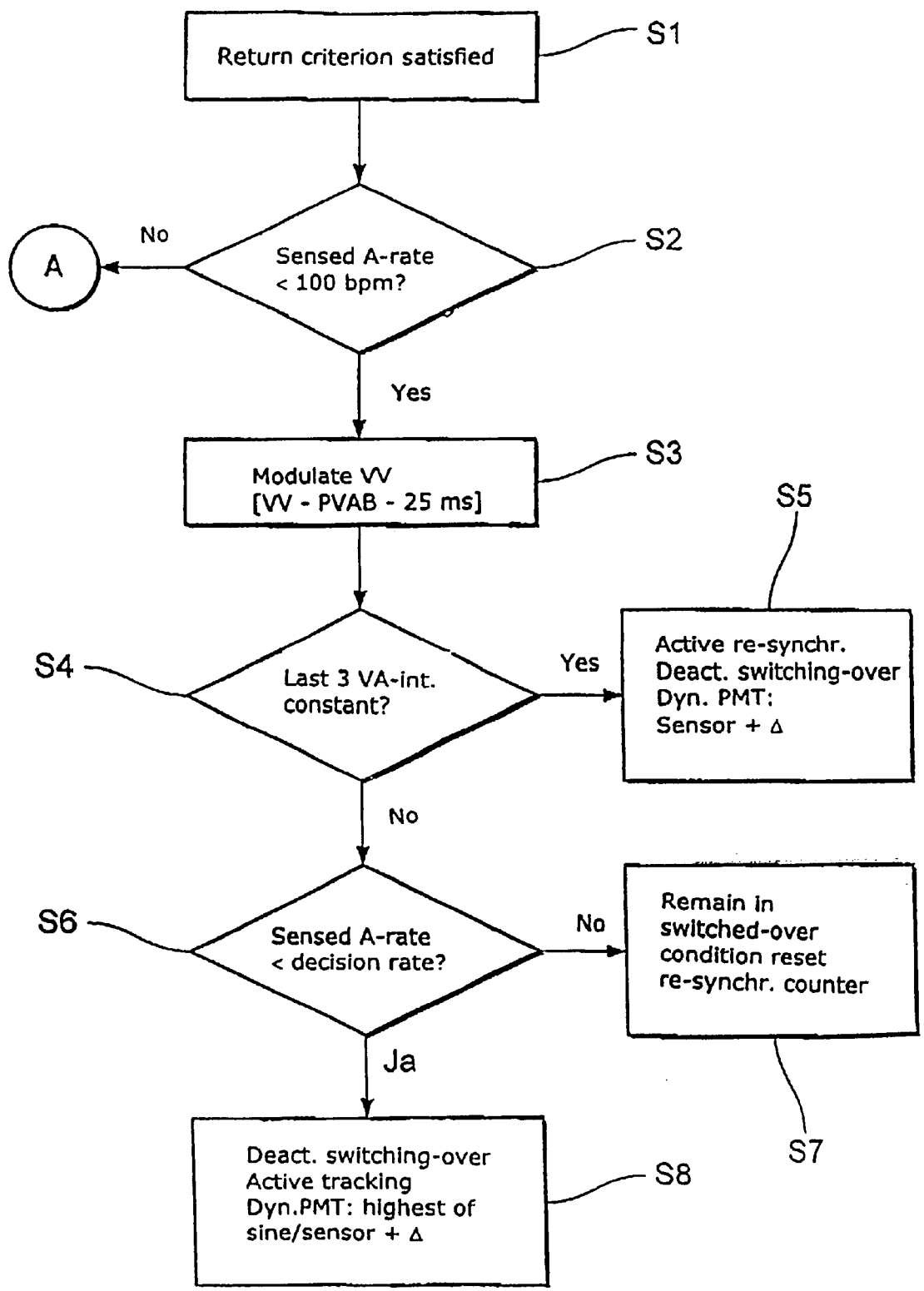
FIG. 2 shows a flow chart relating to operation of an embodiment of a dual-chamber pacemaker according to the invention.

A flow chart outlining the operation of the dual-chamber pacemaker 100 is provided in FIG. 2. First, in step S1, a signal sequence pattern or index for the termination of atrial tachycardia is detected. Thereupon it is established in a step S2 whether the atrial rate is below an arbitrary first rate limit value (here 100 bpm). If the atrial rate is above the first rate limit value, the procedure at branch point 'A' transfers to the subroutine outlined in FIG. 2a. In contrast, of the atrial rate is below the first rate limit value, then for a predetermined number of ventricle stimuli the spacing interval or rate thereof is altered in a step S3. More specifically, in the present example the W-interval is reduced by the post-ventricular atrial blanking period (PVAB) and an additional margin of 25 ms. In step S4 spacing interval is monitored to determine if three VA-intervals have remained constant after the variation in the W-interval.

If three VA-intervals have remained constant, then the detected atrial rate is attributed to a retrograde transfer, the switching-over condition, which is adopted by virtue of vestibule flutter, is deactivated in a step S5 and the pacemaker is actively re-synchronized to atrial activity. In this case, dynamic rate limitation ('dyn. PMT') is effected, which is oriented to the sensor-indicated rate.

In contrast, if the VA-intervals have not remained constant, then the detected atrial rate is compared to a second limit value ('decision rate'—in accordance with the criteria listed hereinbefore, 60 bpm) in step S6. If the atrial rate is equal to or higher than the decision rate, then the circuit assumes that the preceding test involved a 2:1-detection of an atrial rate, which was actually above the decision rate. Accordingly, the pacemaker remains in the asynchronous switched-over condition and at the same time the switching-over or re-synchronization counter is reset to zero in step S7.

Alternatively, if the detected atrial rate is below the decision rate limit value, the pacemaker is switched-over and returns to the synchronous mode in step S8, in which case dynamic ventricular rate limitation is oriented to the higher rate of the sine rate and the sensor-indicated rate.

Figure 2A:
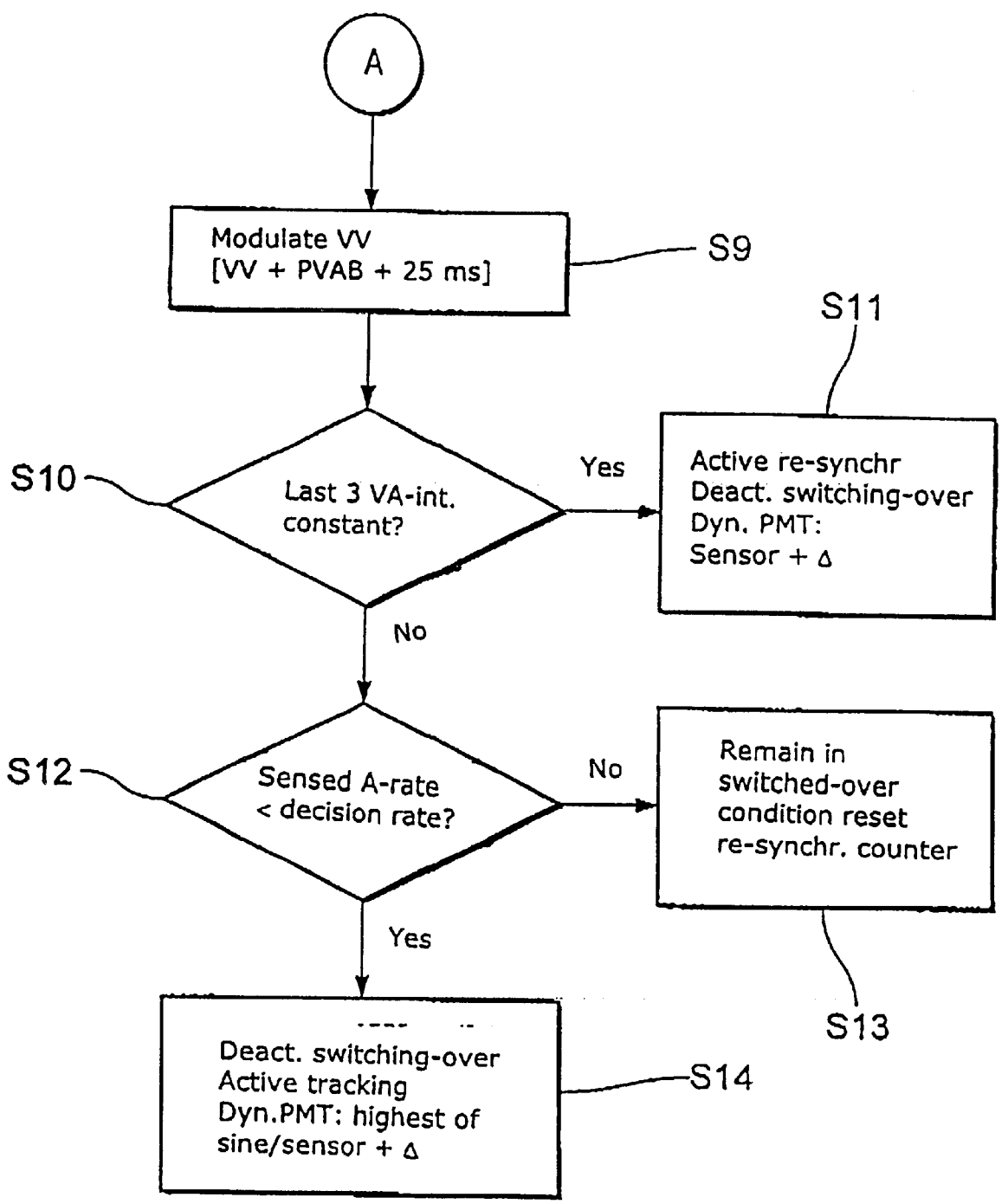
FIG. 2a shows a subroutine of the flow chart shown in FIG. 2.

FIG. 2a outlines the high atrial rate subroutine according to one embodiment of the present invention. Starting from the field 'A' in FIG. 2, in steps S9 to S14, a subroutine similar to the procedure shown in FIG. 2 is implemented. However, the subroutine starts in step S9 with a different kind of variation in the VV-intervals, namely with an increase in the length of the intervals by the PVAB plus an additional interval of 25 ms. Steps S10 to S14 are then identical to steps S4 to S8, described above.

Figure 3:
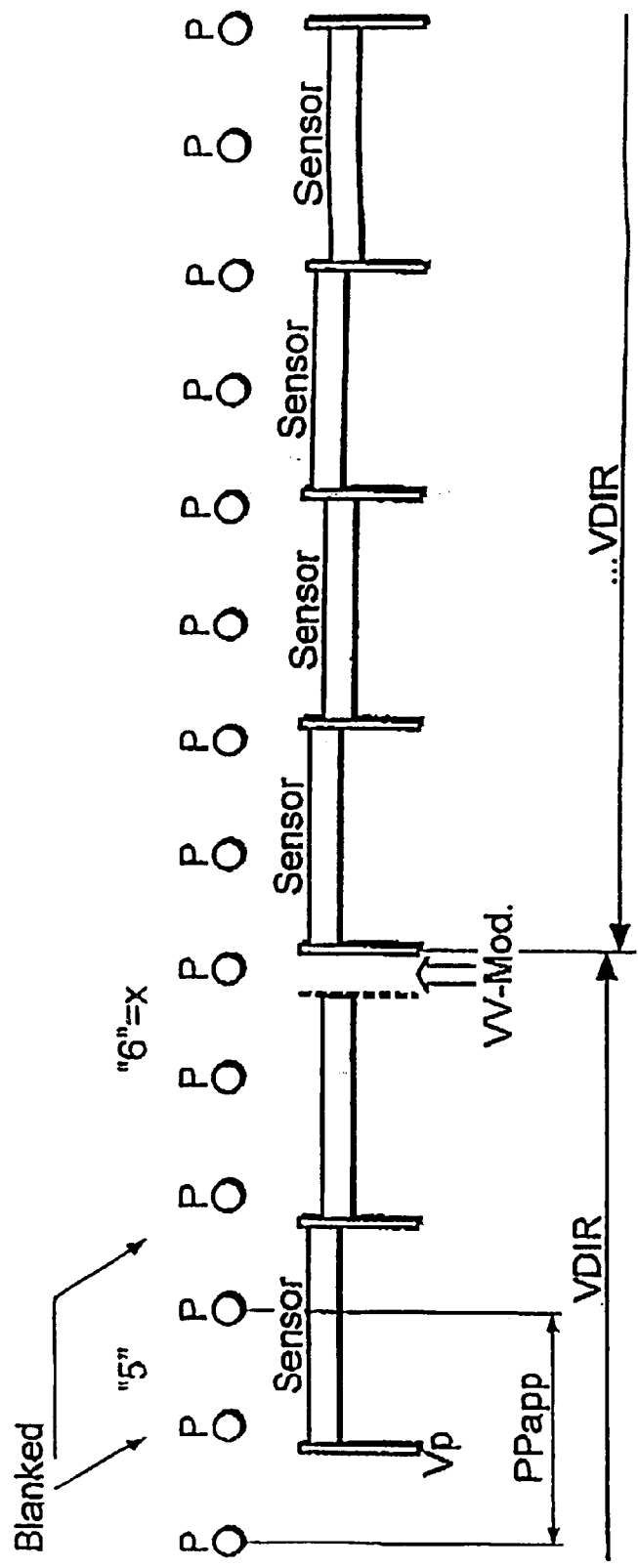
FIG. 3 shows a timing diagram relating to a step in a test procedure according to the invention.

FIG. 3 depicts a schematic timing diagram of the above-described procedure. Shown in the left-hand part of the diagram is the end phase of a conventional x-out of-y-test for switching back from the asynchronous mode (VDIR) into the synchronous mode in which the count values 5 and 6 of the cardiac cycles are reached, and in which apparently a switching-back criterion is satisfied, i.e., the atrial rate is below the decision rate. However, in reality each second one of the atrial activities P is blanked shortly after the ventricle stimulus Vp such that the actions detected by the atrial sensing unit, on the basis of the 2:1-perception, have an apparent spacing PPapp, which simulates termination of vestibule flutter.

In contrast, in the operation of a pacemaker according to the present invention, after attainment of the counter condition 6, which is predetermined as 'x', re-synchronization is not effected straightaway, but firstly the above-discussed W-modulation test is effected and—as this (presumably) shows the continuance of the atrial tachycardia—stimulation is continued in the VDIR-mode. That avoids a 2:1 block behaviour which would inevitably occur without the additional test. Although this additional checking operation requires at most an additional test cycle in comparison with the conventional x-out of-y-rate criterion before re-synchronization can be effected, there is a substantial decrease in the likelihood that the pacemaker will be inappropriately switched back into the synchronous mode, consequently decreasing the likelihood of a PMT.

Figure 4:
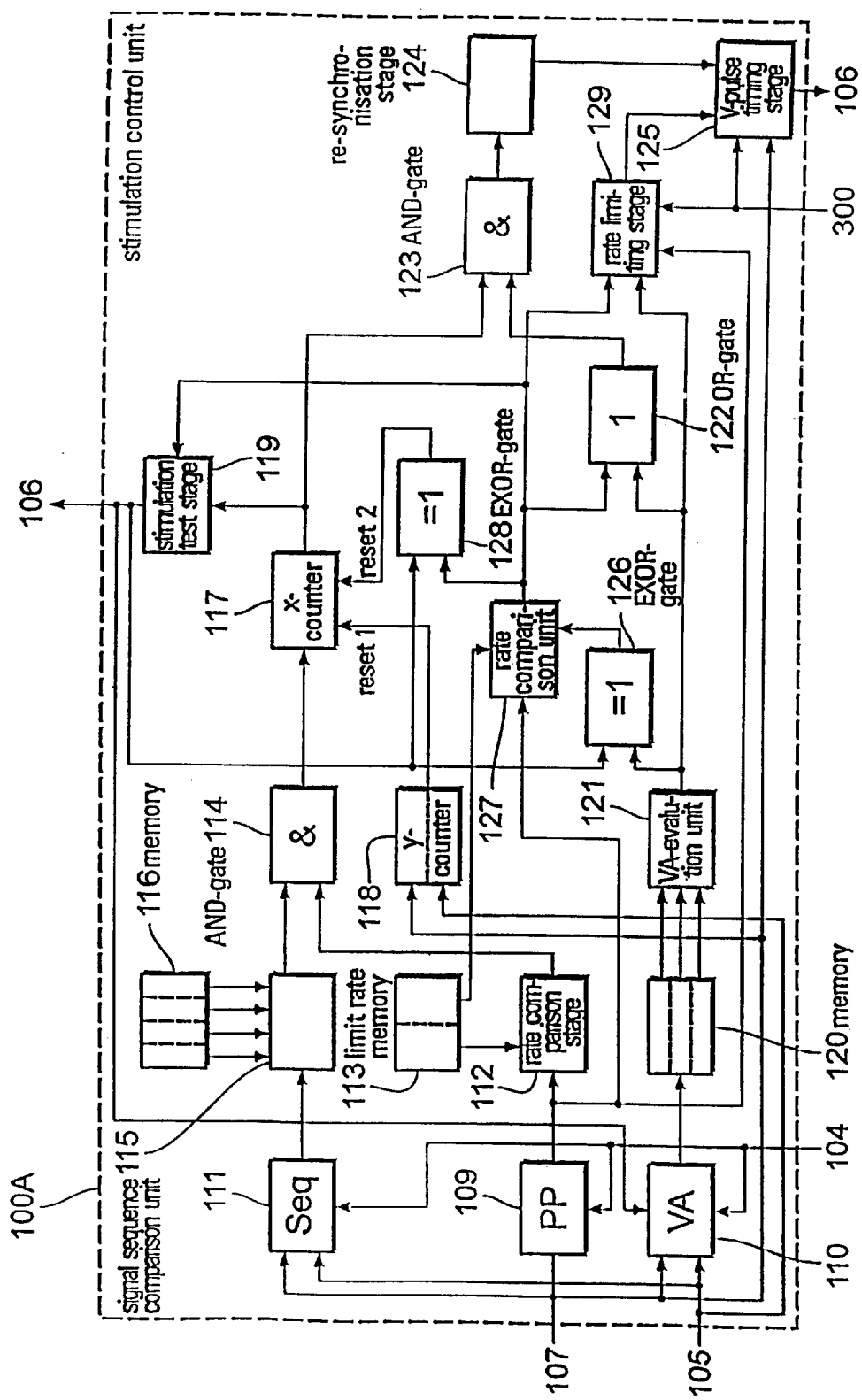
FIG. 4 shows a functional block circuit diagram of an embodiment of the stimulation control unit of a pacemaker according to the invention.

FIG. 4 shows a schematic functional block circuit diagram of the stimulation control unit 100A according to one embodiment of the current invention. It will be understood that the structure of the unit 100A is simplified in the interests of greater ease of understanding of the stimulation control unit 100A in an embodiment of the invention. Although the functional components of the pacemaker 100 of the current invention are shown structurally in FIGS. 1 and 4, it should be understood that the $_{13}$ functional components serving to carry the invention into effect are in practice implemented at least in part in software terms and are inseparably interwoven with the rest of the pacemaker structure.

The stimulation control unit 100A includes a PP-interval or rate calculation stage 109 connected to the output of the atrium sensing unit 107, a VA-interval calculation stage 110 connected to the outputs of the atrium sensing unit 107 and the ventricle sensing unit 105, and a sequence determination stage 111 also connected on the input side to the sensing units 105 and 107 for registration of the succession of cardiac activities in the atrium and the ventricle. The stages 109 and 110 are each also connected to the timer 104 (FIG. 1), which supplies the time signals required for the interval or rate calculations and signal sequence determination.

Connected to the output of the PP-interval calculation stage 109 is a rate comparison stage 112 whose second input is connected to the first memory region of a dual-region limit rate memory 113, and in which a comparison is made between the ascertained current atrial rate and a first limit rate ('decision rate'). In the result thereof, when the rate is below a limit rate, there appears an output signal which is passed to an input of an AND-gate 114.

The output of the sequence determination stage 111 is connected to an input of a signal sequence comparison unit 115 whose second input is connected to a signal sequence pattern memory 116 and whose output goes to the second input of the AND-gate 114. The output of the AND-gate clocks an x-counter 117. The counter 117 has two reset inputs of which one is connected to the output of a y-counter stage 118, which in turn is connected at its input side to the sensing units 105 and 107. The assignment of the second reset input is described hereinafter.

The so-called 'x-out of-y-counting procedure' is implemented with the above-mentioned functional blocks 109 and 111 through 118, with parallel application of a PP-rate criterion and a signal sequence criterion corresponding to the first two of the criteria set forth in Table 1, with regard to the termination of an atrial tachyarhythmia (to which the description herein is to be limited in simplifying fashion). In each of y successive cardiac cycles, which are counted in the counter stage 118, a check is made comparing the identity of the detected signal sequence with a signal sequence pattern previously stored in the memory 116, and comparing the atrial rate to a decision rate stored in the memory 113, and if both criteria are satisfied, the x-counter 117 is incremented. As soon as it has reached the value x, an output signal indicating the positive result of the checking procedure is outputted. In the embodiment illustrated in FIG. 4, it is assumed by way of simplification that the x-counter 117 is reset to zero when the y-counter 118 is running before attaining the count value x and a new checking cycle is started. In practice, however, a sliding x-out of y-counting procedure with rejection of the 'respective 'oldest' cardiac cycle based on the FIFO-principle will be more desirable. as it permits a faster reaction on the part of the pacemaker.

The output of the x-counter 117 is connected to a stimulation test stage 119 for influencing the spacing of a pre-programmed number of ventricle stimuli. The precise mode of influencing that spacing is set by way of a control input of the stage 119, described below. In addition to the ventricle stimulation unit 106, the output of the stimulation test stage is connected to a control input of the VA-calculation stage 110, which triggers the determination of the current VA-intervals and the transfer of those intervals into a VA-interval memory 120 shortly before initiation of the above-mentioned modulation test. The memory 120 is connected to the input of a VA-evaluation unit 121 in which the VA-intervals stored during the modulation test are checked for constancy within a pre-programmed range of fluctuation. If constancy of the VA-intervals is found, a corresponding output signal one ('1') is outputted, otherwise the output remains at zero ('0').

If constancy is found, an activation signal is passed to a switching-over and re-synchronization stage 124 by way of an OR-gate 122 connected on the output side of the VA-evaluation unit 121, and an AND-gate 123 whose second input is connected to the output of the x-counter 117. The stage 124 in turn controls in the atrium-synchronous mode a V-pulse timing stage 125, which in addition is connected on the input side to the atrium sensing unit 107 and the body sensor 300.

In contrast, in the case of a negative outcome of the modulation test, a second PP-rate comparison unit 127 is activated by a test-terminated signal from the stimulation test stage 119 and the '0'-signal at the output of the VA-evaluation stage 121 by way of an EXOR-gate 126, which is connected to those stages. The unit 127 is connected on the input side to the PP-rate calculation stage 109 and the second memory region of the limit rate memory 113, and it checks whether the current atrial rate is below a second pre-programmed limit rate (as shown in FIG. 2:100 bpm). In addition, the unit 127 is also connected to the second input of the above-mentioned OR-gate 122 and by way of same and the AND-gate 123 implements activation of the switching-over and re-synchronization stage 124 when that additional criterion is met. The stage 127 is further connected to a EXOR-gate 128 by way of which, in the presence of the test-terminated signal from the stimulation test stage 119 and a negative outcome in respect of rate checking (output '0' of the stage 127 after a negative outcome of the previous checking for VA-constance), the x-counter 117 is reset to zero by way of its second reset input. Finally, the second rate comparison stage 127 is also connected on its output side to a control input of the stimulation test stage 119, by way of which the modulated interval between the ventricle stimuli is set in dependence on the outcome of the rate checking operation; these steps are summarized in flowchart form as steps S3 and S9 in FIGS. 2 and 2a.

The VA-evaluation stage 121 and the second rate comparison stage 127 are finally connected to control inputs of a rate limiting stage 129, which is connected by way of further inputs to the body sensor 300 and the output of the PP-rate calculation stage 109, and which on the basis of the current atrial rate and the signals from the body sensor and in dependence on the test results (as described above) implements rate limitation for ventricular stimulation.

The invention is not limited in terms of carrying it into effect to the preferred embodiments set forth hereinbefore. On the contrary a number of alternative configurations are possible, which make use of the illustrated solution even in a design configuration of a different kind.

What is claimed is:
1. A dual-chamber cardiac pacemaker comprising:

atrium sensing means for sensing an electrical activity event in the vestibule and producing an atrium electrical activity signal, and ventricle sensing means for sensing an electrical activity event in the ventricle of a heart and producing a ventricle electrical activity signal;

a timer for detecting the time of the occurrence of the electrical activity event and producing a timer signal;

ventricle stimulation means for producing stimulation pulses and outputting same to the ventricle; and a stimulation control unit for time control of the production and output of the stimulation means, said stimulation means comprising switching means for switching over from an asynchronous to a vestibule-synchronous mode, criterion memory means for the storage of at least one switching-over criterion for mode switching-over, and a processing unit for processing signals from the atrium sensing means, the ventricle sensing means and the timer and for checking fulfilment of the switching-over criterion, wherein:

the criterion memory means has a signal sequence memory for storage of a predetermined selection of signal sequence patterns, the signal sequence patterns including electrical activity events reflecting the electrical activity of the heart selected from the group consisting of: signals from the atrium sensing means and the ventricle sensing means, signals from the ventricle stimulation means, and a time interval criterion which concerns the spacing between two atrially sensed events and signals from an atrially sensed event in relation to a ventricular activity event, the processing unit has comparison means for comparing the electrical activity events sensed by the atrium sensing means and the ventricle sensing means in a plurality of successive cardiac cycles to the stored signal sequence patterns, the signal sequence patterns being stored as follows:
As-V-As wherein As-As>1.000 ms
V-As-As-V wherein As-As>1.000 ms
V-V-As wherein V-As>1.000 ms
V-V without interposed As,
wherein: As is an atrially detected event and V is a ventricularly detected or stimulated event, and the stimulation control unit further has counter means connected to the comparison means for counting the number of cardiac cycles in which the electrical activity events sensed by the atrium sensing means and the ventricle sensing means is the same as one of the pre-stored signal sequence patterns within a predetermined total number of successive cardiac cycles and produce a representative output signal, the counting means being in signal communication with a control input of the switching means such that when the switching means receives the output signal from the counting means the switching means switches between the asynchronous and the vestibule-synchronous modes;

wherein the stimulation control unit further comprises a test device having an output for outputting a test signal and a logic stage having at least one input, wherein the test device is designed to carry out, evaluate, and signal the results of an active test for the presence of retrograde transfer, the output of the test device being connected to the at least one input of the logic stage, the logic stage being connected between the counter means and the switching means, such that switching of the switching means depends on the presence of an output signal from the counter means and an output signal from the test device, indicating a positive test result; and wherein the test device has modulation means for producing a predetermined modulation of the time spacing of successive ventricle stimuli, VA-detection means for detecting and storing a plurality of VA-time intervals between a respective ventricle stimulus and a subsequent atrial activity, and VA-evaluation means for comparative evaluation of the VA-time intervals as a reaction to modulation of the time spacing of the ventricle stimuli.

2. The dual-chamber cardiac pacemaker as set forth in claim 1 wherein the modulation means are adapted for an increase or reduction in length of the time spacings by a predetermined amount, and the VA-evaluation means output an output signal only when at least three successive VA-time intervals were constant after modulated ventricle stimuli.

3. The dual-chamber cardiac pacemaker as set forth in claim 2, wherein the predetermined amount is equal to a post-ventricular atrial blanking time and an additional increment.

4. The dual-chamber cardiac pacemaker as set forth in claim 1 wherein the criterion memory means are adapted for the storage of at least one rate limit value concerning the time intervals between successive atrial activities as a stored rate threshold value, and the processing unit has a calculation unit for ascertaining the current atrial time intervals or atrial rate and a rate comparison unit for comparison thereof with the stored rate threshold value.

5. The dual-chamber cardiac pacemaker as set forth in claim 4 wherein the rate comparison unit is designed to produce an output signal and is connected to the at least one input of the logic stage in such a way that switching of the switching means upon application of the output signal from the counter means further depends on the additional presence of the output signal from the rate comparison unit.

6. The dual-chamber cardiac pacemaker as set forth in claim 5 further comprising an OR-gate and an AND-gate having at least one input and wherein the logic stage contains the OR-gate, the OR-gate being connected to the at least one input of the AND-gate and wherein the outputs of the test device and the rate comparison unit are connected to the at least one input of the logic stage.

7. The dual-chamber cardiac pacemaker as set forth in claim 4, wherein the stored rate threshold value comprises two rate limit values.

8. A dual-chamber cardiac pacemaker comprising:

an atrium sensor designed to sense an electrical activity event in the vestibule and produce an atrium electrical activity signal, and a ventricle sensor to sense an electrical activity event in the ventricle of a heart and produce a ventricle electrical activity signal;

a timer designed to detect the time of the occurrence of the electrical activity event and produce a timer signal;

a ventricle stimulator designed to generate stimulation pulses and output same to the ventricle; and a stimulation control unit designed to time control the production and output of the stimulator, said stimulator comprising a switch designed to switch from an asynchronous to a vestibule-synchronous mode, a criterion memory designed to store at least one switching-over criterion for mode switching-over, and a processor designed to process signals from the atrium sensor, the ventricle sensor and the timer and for checking fulfilment of the switching-over criterion, wherein:

the criterion memory has a signal sequence memory designed to store a predetermined selection of signal sequence patterns, the signal sequence patterns including electrical activity events reflecting the electrical activity of the heart selected from the group consisting of: signals from the atrium sensing means and the ventricle sensing means, signals from the ventricle stimulation means, and a time interval criterion which concerns the spacing between two atrially sensed events and signals from an atrially sensed event in relation to a ventricular activity event, the processor has a comparator designed to compare the electrical activity events sensed by the atrium sensor and the ventricle sensor in a plurality of successive cardiac cycles to the stored signal sequence patterns, the signal sequence patterns being stored as follows:
As-V-As wherein As-As>1.000 ms
V-As-As-V wherein As-As>1.000 ms
V-V-As wherein V-As>1.000 ms
V-V without interposed As,
wherein: As is an atrially detected event and V is a ventricularly detected or stimulated event, and the stimulation control unit further has a counter connected to the comparator designed to count the number of cardiac cycles in which the electrical activity events sensed by the atrium sensor and the ventricle sensor are the same as one of the pre-stored signal sequence patterns within a predetermined total number of successive cardiac cycles and produce a representative output signal, the counter being in signal communication with a control input of the switch such that when the switch receives the output signal from the counter the switch switches between the asynchronous and the vestibule-synchronous modes wherein the stimulation control unit further comprises a test device having an output for outputting a test signal and a logic stage having at least one input, wherein the test device is designed to carry out, evaluate, and signal the results of an active test for the presence of retrograde transfer, the output of the test device being connected to the at least one input of the logic stage, the logic stage being connected between the counter and the switch, such that switching of the switch depends on the presence of an output signal from the counter and an output signal from the test device, indicating a positive test result; and wherein the test device has a modulator for producing a predetermined modulation of the time spacing of successive ventricle stimuli, a VA-detector for detecting and storing a plurality of VA-time intervals between a respective ventricle stimulus and a subsequent atrial activity, and a VA-evaluator for comparative evaluation of the VA-time intervals as a reaction to modulation of the time spacing of the ventricle stimuli.

* * * * *